United States Patent [19]

Szántay et al.

[11] Patent Number: 4,735,946
[45] Date of Patent: Apr. 5, 1988

[54] EBURNANE DERIVATIVES, PROCESS FOR THEIR PREPARATION AND PHARMACEUTICAL COMPOSITIONS CONTAINING THEM

[75] Inventors: Csaba Szántay; Lajos Szabó; György Kalaus; János Kreidl; Mária Farkas née Kirják; László Czibula; Béla Stefkó; György Visky; Judit Mészáros née Brill, all of Budapest, Hungary

[73] Assignee: Richter Gedeon Vegyeszeti Gyar Rt., Budapest, Hungary

[21] Appl. No.: 718,917

[22] Filed: Apr. 2, 1985

[30] Foreign Application Priority Data

Apr. 2, 1984 [HU] Hungary ............... 1323/84

[51] Int. Cl.$^4$ ............... A61K 31/44; C07D 461/00
[52] U.S. Cl. ............... 514/283; 546/51
[58] Field of Search ............... 546/51; 514/283

[56] References Cited

U.S. PATENT DOCUMENTS

| 3,753,995 | 8/1973 | Martel et al. ............... 546/51 |
| 4,464,535 | 8/1984 | Szántay et al. ............... 546/51 |
| 4,549,020 | 10/1985 | Szántay et al. ............... 546/51 |
| 4,551,462 | 11/1985 | Szántay et al. ............... 514/283 |

FOREIGN PATENT DOCUMENTS

| 00168197 | 1/1986 | European Pat. Off. ............... 546/51 |
| 2085630 | 12/1971 | France ............... 514/283 |
| 0111484 | 8/1980 | Japan ............... 514/283 |
| 2123413 | 2/1984 | United Kingdom ............... 546/51 |
| 2,124,215 | 2/1984 | United Kingdom ............... 546/51 |
| 2124216 | 2/1984 | United Kingdom ............... 546/51 |

Primary Examiner—Donald G. Daus
Assistant Examiner—Diana G. Rivers
Attorney, Agent, or Firm—Karl F. Ross; Herbert Dubno; Jonathan Myers

[57] ABSTRACT

The invention relates to new eburnane derivatives of the formula (I)

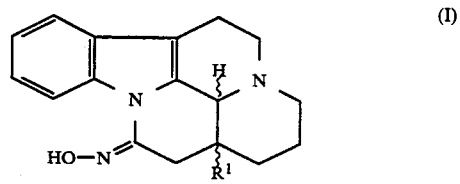

wherein
R$^1$ is alkyl having from 1 to 6 carbon atoms, and acid addition salts thereof.

The invention further relates to a process for the preparation of these compounds and pharmaceutical compositions containing them.

Compounds of formula (I) show remarkable CNS-activity and are useful intermediates in the preparation of other, pharmaceutically active compounds.

16 Claims, No Drawings

EBURNANE DERIVATIVES, PROCESS FOR THEIR PREPARATION AND PHARMACEUTICAL COMPOSITIONS CONTAINING THEM

The invention relates to new eburnane derivatives, a process for their preparation and pharmaceutical compositions containing them. More particularly, the invention concerns new racemic and optically active 14-hydroxyimino-eburnane derivatives of the formula (I)

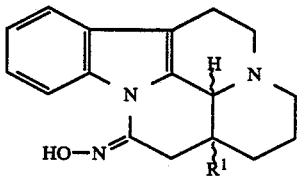
(I)

wherein
$R^1$ is alkyl having from 1 to 6 carbon atoms, and acid addition salts thereof.

According to another aspect of the invention there is provided a process for the preparation of the compunds of formula (I) by oxidizing a racemic or optically active (hydroxyiminoethyl)-octahydro-indolo[2,3-a]quinolizine derivative of the formula (II)

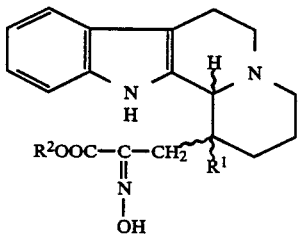
(II)

wherein
$R^1$ is as defined above and
$R^2$ is hydrogen or alkyl having from 1 to 6 carbon atoms, or the metal salts or acid addition salts thereof in an alkaline medium, and if desired, treating the compound obtained with an acid and/or resolving same.

By the process according to the invention both racemic and optically active compounds of the formula (I) can be prepared, and in the formula the hydrogen in the 3-position and the $R^1$ substituent in the 16-position may have an ($\alpha,\alpha$), ($\beta,\beta$), ($\alpha,\beta$) or ($\beta,\alpha$) configuration. The stereo- and geometrical isomerism of the compounds of formula (I), as well as their optical activity are the function of the corresponding properties of the starting compounds of formula (II), and these charcteristics are transmitted from the starting compounds into the products of formula (I) unchanged. For instance, if racemic compounds of formula (II) are used as starting material, racemic compounds of formula (I) are obtained, while starting from optically active compounds of formula (II) optically active compounds of formula (I) may be prepared. Moreover, if in the starting compound of the formula (II) the hydrogen in the 3-position and the $R^1$ substituent in the 16-position have an ($\alpha,\alpha$), ($\beta,\beta$), ($\alpha,\beta$) and ($\beta,\alpha$) configuration, respectively, the corresponding atoms and groups, respectively will have the same configuration in the end products prepared therefrom.

Racemic and optically active compounds of formula (I) are new and pharmaceutically active, in particular show remarkable CNS-activity. According to a yet further aspect of the invention there are provided pharmaceutical compositions comprising, as active ingredient, at least one compound of formula (I) as hereinbefore defined or a physiologically compatible acid addition salt thereof in association with a pharmaceutical carrier or excipient.

The compounds of formula (I) are further valuable intermediates in the preparation of other pharmaceutically active compounds having eburnane skeleton, such as eburnamonines.

In the above formulae $R^1$ and $R^2$ as an alkyl group having from 1 to 6 carbon atoms may represent any straight-chained or branched $C_{1-6}$ alkyl group, e.g. a methyl, ethyl, n-propyl, isopropyl, n-butyl, isobutyl, tert.-butyl, n-pentyl, isopentyl, n-hexyl or isohexyl group. As metal salts of the starting compounds for example alkali metal salts, e.g. lithium, potassium, sodium salts, or alkaline earth metal salts, e.g. calcium, magnesium, etc. salts can be used.

As acid addition salts of the starting compounds for example salts formed with the following acids may be used. Inorganic acids, such as hydrogen halides, e.g. hydrochloric and hydrobromic acids, sulfuric acid, phosphoric acid, perhaloacids, e.g. perchloric acid, etc. Organic acids, such as formic acid, acetic acid, propionic acid, glycolic acid, maleic acid, hydroxymaleic acid, fumaric acid, succinic acid, tartaric acid, ascorbic acid, citric acid, malic acid, salicyclic acid, lactic acid, cinnamic acid, benzoic acid, phenylacetic acid, p-amino-benzoic acid, p-hydroxy-benzoic acid, p-amino-salicylic acid, etc., cycloaliphatic sulfonic acids, e.g. cyclohexylsulfonic acid; arylsulfonic acids, e.g. p-toluene-sulfonic acid, naphthenesulfonic acid, sulfanilic acid, etc.; amino acids, e.g. asparaginic acid, glutamic acid, N-acetyl-asparaginic acid, N-acetyl-glutaric acid, etc.

The starting compounds of the formula (II) may for example be prepared according to the Belgian Patent Specification No. 893,492 by reduction and nitrozation of a racemic or optically active hexahydroindolo[2,3-a]quinolizine.

The oxidation according to the invention may for example be performed by passing oxygen or an oxygen-containing inert gas mixture, e.g. air, nitrogen, noble gases, e.g. argon, neon, helium through the reaction mixture. Alternatively, a chemical oxidation agent may also be employed. Chemical oxidating agents include for example hydrogen peroxide, organic or inorganic peroxides, e.g. coumol peroxide, paracids, persulfates, etc. If desired, these percompounds may be used simultaneously with oxygen, air or another inert gas mixture containing oxygen. If desired, in the process according to the invention as a catalyst a heavy metal with varying valence, such as copper, iron, manganese, cobalt, chromium, tungsten, vanadium, silver, etc. may be used in the form of its salts with an organic or inorganic acid, hydroxides, oxides or complexes, e.g. "Complexon" (ethylenediaminetetraacetic acid). The catalysts are preferably employed in an amount of $10^{-1}$ to $10^{-3}$ molar equivalent, if oxidation is carried out with air, an oxygen-containing inert gas mixture or with inorganic or organic percompounds. If, however, these heavy metal compounds are employed alone, they should be used in an at least equimolar amount. If oxidation is performed by the aid of air, an oxygen-containing inert gas mixture or percompounds, in addition to the heavy metal compounds, as a catalyst also other organic materials taking part in the redox processes, such as hydroquinone, pirocatechine, etc. may be used. The amount of these compounds may exceed the catalytic amount. According to an embodiment of the instant process the oxidation is carried out with a percompound, in the presence of a catalytic amount of a heavy metal compound. In addition to the percompounds for example alkali metal hypohalides, e.g. sodium hypochloride can also be used as oxidation agents in the process according to the invention.

In the oxidation process according to the invention as a basic medium for example an alkali metal or alkaline earth metal hydroxide can be used, preferably as a solution in water or in a mixture of a water-miscible solvent and water. As a water-miscible solvent, for example protic solvents, such as mono- or polyfunctional alcohols, glycols or glycol ethers, such as ethylene glycol, diethylene glycol, diethylene glycol monoalkyl ethers, or dipolar aprotic solvents, such as ketones, e.g. acetone, methylethyl ketone, methylisobutyl ketone, dimethyl formamide, dimethyl sulfoxide, acetonitrile may be employed. The base is preferably used in an amount which adjusts the pH to 10 to 14.

The process according to the invention is carried out at a temperature between 60° C. and 150° C., preferably 90° C. and 110° C.

The pressure generally is between 1 and 10 atm, it is, however, preferred to perform the reaction under atmospheric pressure.

The reaction time is a function of the oxidizing agent, catalyst, temperature and pressure employed, and preferably is between 5 minutes and 4 hours. During this time the reaction according to the invention takes place almost quantitatively, and the product precipitates in a crystalline form which is easy to separate from the reaction mixture.

According to a preferred embodiment of the process according to the invention a racemic or optically active compound of the formula (II) or a metal salt or acid addition salt thereof is admixed with a five-fold molar amount of an aqueous sodium hydroxide solution, and air is passed through the mixture at 90° to 100° C. The mixture contains also a catalytic amount of a heavy metal salt.

The product provided by the process according to the invention is obtained in a high purity. The purity, i.e. the active ingredient content of the product were controlled by high pressure liquid chromatography (HPLC). The purity generally is between 91 and 97%.

The compounds of the formula (I), prepared according to the above-described process may, if desired, be further purified, e.g. by recrystallization, using protic or aprotic dipolar solvents. Suitable solvents include cyclic ethers, such as dioxane, tetrahydrofurane.

The structure of the new compounds of formula (I) is unambiguously verified by the results of NMR and mass spectrometrical measurements.

The compounds of formula (I), when administered in a dose of 15 to 30 mg/kg show anticonvulsive activity, while they are devoid of neurotoxic side-effects and do not potentiate hexobarbital.

The pharmacological activity of the instant compounds was tested on CFLP (LATI) male mice weighing 18 to 22 g each. The test compounds were administered in a 0.01% solution with ascorbic acid orally, through a tube, one hour before the experiment.

The foollowing test methods have been employed: maximum electroshock (Swinyard E. A. et al: J. Pharmacol. Exp. Ther. 106, 319 (1952)); antimetrazole effect (Everett G. M. and Richards R. K.: J. Pharmacol. Exp. Ther. 81, 402 (1944)); hexobarbital potentiation (Rümke L. et al: Arch. Int. Pharmacodyn. 146, 10 (1963)); muscle coordination (Kinnord W. J. and Cors C. F.: Brit. J. Pharmacol. 121, 354 (1957)).

The compounds of the formula (I) may be formulated for therapeutic purposes. The invention therefore relates also to pharmaceutical compositions comprising as active ingredient at least one compound of formula (I), in association with pharmaceutical carriers and/or excipients. Carriers conventional for this purpose and suitable for parenteral or enteral administration as well as other additives may be used. As carriers for example water, gelatine, lactose, starch, pectine, magnesium stearate, stearic acid, talc, vegetable oils, e.g. peanut oil, olive oil, etc. can be used. The compound can be formulated as conventional pharmaceutical formulations, for example in a solid (globular and angular pills, dragées, e.g. hard gelatine capsules) or liquid (injectable oily or aqueous solutions or suspensions, emulsions, syrups, soft gelatine capsules, injectable oily or aqueous solutions or suspensions, etc.) form. The quantity of the solid carrier can be varied within wide ranges, but preferably is between 25 mg and 1 g. The compositions optionally contain also other conventional pharmaceutical additives, such as preserving agents, stabilizing agents, wetting agents, emulsifying agents, salt for adjusting the osmotic pressure, buffers, flavoring and odoring substances. The compositions optionally contain also other pharmaceutically active ingredients. The formulations are preferably prepared in dose units corresponding to the route of administration desired. Pharmaceutical compositions are prepared by conventional techniques, e.g. by sieving the ingredients, admixing, granulation and pressing or dissolution. The formulations, if desired, may be subjected to further usual treatments, e.g. sterilization.

The invention is elucidated in detail by the aid of the following non-limiting Examples.

EXAMPLE 1

(−)-14-Hydroxyimino-eburnane (α,16α)

3.57 g (0.01 mole) of (−)-1α-ethyl-1β-(2'-carboxy-2'-hydroxyiminoethyl)-1,2,3,4,6,7,12,12,bα-octahydro-indolo[2,3-a]quinolizine, 50.0 ml of water and 2.0 g (0.05 mole) of solid sodium hydroxide are heated into 90° C. under vigorous stirring, whereupon air is passed through the reaction mixture for two hours. The reaction mixture is then cooled to room temperature, the precipitated product is filtered off, washed with two 5-ml portions of water and dried.

2.9 g of the title compound are obtained.
Yield: 94.0%
Melting point: 285° to 288° C.
Purity: 95.5% (determined by HPLC)
$[\alpha]_D^{20} = -44.2°$ (c=1, 8:2 mixture of chloroform and methanol)

The obtained product (2.9 g) is dissolved in 43.5 ml of hot dioxane, the solution is cooled to 10° C., and the precipitated substance is filtered off.

2.65 g of pure compound are obtained.
Total yield: 86%
Purity: 99.2% (HPLC)
Melting point: 292° to 294° C.

$[\alpha]_D^{20} = -42.1°$ (c=1, 8:2 mixture of chloroform and methanol)

NMR spectrum (DMSO-$d_6$): =0.65 t(3), 0.4–3.2 m skeleton CH$_2$-k, 3.6 d (1), 6.9–7.5 m (3) aromatic, 8–8.3 m (1) aromatic, 10.03 s(1) N=OH (exchangable with $D_2O$).

Mass spectrum (200° C.) m/e: M+309, 308, 293, 292, 264, 170, 141, 115.

EXAMPLE 2

(−)-14-Hydroxyimino-eburnane (3α,16α)

A mixture of 4.075 g (0.01 mole) of (−)-1α-ethyl-1β-(2+-methoxycarbonyl-2'-hydroxyiminoethyl)-1,2,3,4,6,7,12,12bα-octahydroindolo[2,3-a]quinolizine hydrogen chloride, 45.0 ml of water and 1.6 g (0.04 mole) of solid sodium hydroxide is heated up to 92° to 96° C. under stirring. Thereafter air is passed through the reaction mixture for 1.5 hours. The reaction mixture is then cooled to room temperature, the precipitated crystals are filtered off, washed with two 5-ml portions of water and dried.

2.87 g of the title compound are obtained.
Yield: 93%
Melting point: 286° to 288° C.
Purity: 95.9%
$[\alpha]_D^{20} = -43.9°$ (c=1, 8:2 mixture of chloroform and methanol)

EXAMPLE 3

(+)-14-Hydroxyimino-eburnane (3α,16β)

Through a mixture of 3.57 g (0.01 mole) of (+)-1β-ethyl-1α-(2'-carboxyl-2'-hydroxyiminoethyl)-1,2,4,6,12,12bβ-octahydroindolo[2,3-a]quinolizine, 50.0 ml of water, 2.0 g (0.05 mole) of solid sodium hydroxide and 0.049 g (0.0002 mole) of manganese(II)acetate tetrahydrate air is passed under stirring at 80° C. for one hour.

The reaction mixture is further treated as described in Example 1.

2.98 g of the desired compound are obtained.
Yield: 96.5%
Purity: 94.5%
$[\alpha]_D^{20} = +43.5°$ (c=1, 8:2 mixture of chloroform and methanol)

EXAMPLE 4

(+)-14-Hydroxyimino-eburnane(3α,16β)

Air is passed through a mixture of 3.57 g (0.01 mole) of (−)-1α-ethyl-1β-(2'-carboxyl-2'-hydroxyiminoethyl)-1,2,3,4,6,7,12,12bβ-octahydroindolo[2,3-a]quinolizine, 45.0 ml of water, 5.0 ml of ethylene glycol, 1.6 g of solid sodium hydroxide and 0.1 g (0.0005 mole) of copper(II)acetate hydrate under stirring at 95° to 98° C. for one hour.

The reaction mixture is further treated as described in Example 1.

2.79 g of the aimed compound are obtained.
Yield: 90.6%
Purity: 93.8%
Melting point: 253° to 255° C.
$[\alpha]_D^{20} = +77.5°$ (c=1, 8:2 mixture of chloroform and methanol)

EXAMPLE 5

(−)-14-Hydroxyimino-eburnane (3β,16α)

Air is passed through a mixture of 3.71 g (0.01 mole) of (+)-1β-ethyl-1α-(2'-methoxycarbonyl-2'-hydroxyimino)-1,2,3,4,6,7,12,12bα-octahydroindolo[2,3-a]quinolizine, 10.0 ml of water, 40.0 ml of ethylene glycol, 2.0 g (0.05 mole) of solid sodium hydroxide and 0.1225 g (0.0005 mole) of manganese(II)acetate tetrahydrate under stirring at a temperature of 105° to 110° C. for half an hour. Thereafter 50.0 ml of water are added to the mixture, which is then treated as described in Example 1.

2.71 g of the desired compound are obtained.
Yield: 87.8%
Purity: 92.9%
Melting point: 252° to 254° C.
$[\alpha]_D^{20} = -78.7°$ (c=1, 8:2 mixture of chloroform and methanol)

EXAMPLE 6

(−)-14-Hydroxyimino-eburnane (3α,16α)

To a mixture of 3.57 g (0.01 mole) of (−)-1α-ethyl-1β-(2'-carboxyl-2'-hydroxyiminoethyl)-1,2,3,4,6,7,12,12bα-octahydroindolo[2,3-a]quinolizine, 60.0 ml of water and 1.6 g (0.04 mole) of solid sodium hydroxide 1.36 g (0.012 mole) of a 30% aqueous hydrogen peroxide solution are added at 90° C., in one hour, whereupon the mixture is stirred at the same temperature for two additional hours.

The reaction mixture is further treated as described in Example 1.

2.47 g of the desired compound are obtained.
Yield: 80.0%
Purity: 92.0%
Melting point: 278° to 282° C.
$[\alpha]_D^{20} = -45.3°$ (c=1, 8:2 mixture of chloroform and methanol)

EXAMPLE 7

(−)-14-Hydroxyimino-eburnane (3α,16α)

Following the procedure described in Example 6 but using 1.25 g (0.011 mole) of a 30% aqueous hydrogen peroxide solution and, in addition, 0.049 g (0.0002 mole) of manganese(II)acetate tetrahydrate, the title compound is obtained. Reaction time: 2 hours.

2.71 g of the desired compound are obtained.
Yield: 88.0%
Purity: 93.5%
Melting point: 280° to 283° C.
$[\alpha]_D^{20} = -44.9°$ (c=1, 8:2 mixture of chloroform and methanol)

EXAMPLE 8

(−)-14-Hydroxyimino-eburnane(3α,16α)

Air is passed through a mixture of 3.57 g (0.01 mole) of (−)-1α-ethyl-1β-(2'-carboxyl-2'-hydroxyiminoethyl)-1,2,3,4,6,7,12,12bα-ocathydroindolo[2,3-a]quinolizine, 50.0 ml of water, 1.6 g (0.04 mole) of solid sodium hydroxide and 0.11 g (0.0001 mole) of hydroquinone with stirring at 85° to 90° C. for three hours.

By treating the reaction mixture as described in Example 1 2.78 g of the desired compound are obtained.
Yield: 90.0%
Purity: 93.2%
Melting point: 280° to 282° C.
$[\alpha]_D^{20} = -45°$ (c=1, 8:2 mixture of chloroform and methanol)

EXAMPLE 9

(−)-14-Hydroxyimino-eburnane (3α,16α)

The procedure described in Example 1 is followed, except that instead of air, oxygen gas is passed through the reaction mixture. The reaction time is one hour, instead of two hours.

2.88 g of the title compound are obtained.
Yield: 93.5%
Purity: 95.0%
Melting point: 282° to 284° C.
$[\alpha]_D^{20} = -44.8°$ (c=1, 8:2 mixture of chloroform and methanol)

EXAMPLE 10

(−)-14-Hydroxyimino-eburnane (3α,16α)

Air is passed through the mixture of 1.5 g (0.004 kmole) of (−)-1α-ethyl-1β-(2'-methoxycarbonyl-2'-hydroxyiminoethyl)-1,2,3,4,6,7,12,12bα-octahydroindolo[2,3-a]quinolizine, 25.0 lit. of water and 0.64 kg (0.016 kmole) of solid sodium hydroxide under a pressure of 4 atm., at a temperature of 95° C. and a rate of 1000 lit./hour for two hours.

By treating the reaction mixture as described in Example 1, 1.12 kg of the desired compound are obtained.
Yield: 91.0%
Purity: 92.4%
Melting point: 279° to 281° C.
$[\alpha]_D^{20} = -45.2°$ (c=1, 8:2 mixture of chloroform and methanol)

EXAMPLE 11

(−)-14-Hydroxyimino-eburnane (3α,16α)

A mixture of 3.71 g (0.01 mole) of (−)-1α-ethyl-1β-(2'-methoxycarbonyl-2'-hydroxyiminoethyl)-1,2,3,4,6,7,12,12bα-octahydroindolo[2,3-a]quinolizine, 60.0 ml of water, 1.6 g (0.04 mole) of solid sodium hydroxide and 3.0 g (0.015 mole) of copper(II)acetate hydrate is stirred at 100° C. for three hours. The mixture is then cooled to room temperature, the precipitated substance is filtered off, washed with two 5-ml portions of water and dried.

The product obtained is dissolved in 40.0 ml of dioxane under boiling. The solution is cooled, the precipitated crystals are filtered off, washed with 3 ml of dioxane and dried.

2.62 g of the desired compound are obtained.
Yield: 85%
Melting point: 282° to 287° C.
Purity: 91.8%
$[\alpha]_D^{20} = -45.3°$ (c=1, 8:2 mixture of chloroform and methanol)

EXAMPLE 12

(±)-cis-14-Hydroxyimino-eburnane

Following the procedure described in Example 2 but starting from 3.71 g (0.01 mole) of (±)-cis-1-ethyl-1-(2'-methoxycarbonyl-2'-hydroxyiminoethyl)-1,2,3,4,6,7,12,12b-octahydroindolo[2,3-a]-quinolizine, the title compond is obtained.
Yield: 2.66 g (86.0%)
Melting point: 278° to 280° C.

EXAMPLE 13

(±)-trans-14-Hydroxyimino-eburnane

Following the procedure described in Example 2 but starting from 3.71 g (0.01 mole) of (±)-trans-1-ethyl-1-(2'-methoxycarbonyl-2'-hydroxyiminoethyl)-1,2,3,4,6,7,12,12b-octahydroindolo[2,3-a]quinolizine, 2.73 g of the title compound are obtained.
Yield: 88.5%
Melting point: 268° to 270° C.

EXAMPLE 14

(−)-14-Hydroxyimino-eburnane (3α,16α)

3.71 g (0.01 mole) of (−)-1α-ethyl-1β-(2'-methoxycarbonyl-2'-hydroxyiminoethyl)-1,2,3,4,6,7,12,12bα-octahydroindolo[2,3-a]quinolizine are admixed with 50.0 ml of water, 2.0 g (0.05 mole) of solid sodium hydroxide and 0.07 g (0.00025 mole) of ethylenediaminetetraacetic acid disodium salt (Komplexon III) and 0.1225 g (0.0005 mole) of manganese(II)acetate tetrahydrate. Air is passed through the mixture at 94° to 96° C. under stirring for 1.5 hours. The mixture is then cooled to room temperature, and is further treated as described in Example 2. 2.83 g of the desired compound are obtained.
Yield: 91.6%
Melting point: 286° to 288° C.
Purity: 95.8%
$[\alpha]_D^{20} = -44.1°$ (c=1, 8:2 mixture of chloroform and methanol)

EXAMPLE 15

(−)-14-Hydroxyimino-eburnane(3α,16α)

A mixture of 3.71 g (0.01 mole) of (−)-1α-ethyl-1β-(2'-methoxycarbonyl-2'-hydroxyiminoethyl)-1,2,3,4,6,7,12,12bα-octahydroindolo[2,3-a]quinolizine, 50.0 ml of water, 2.0 g (0.05 mole) of solid sodium hydroxide, 0.01 g (0.00004 mole) of manganese(II)acetate tetrahydrate is heated up to 90° to 95° C. To the mixture 13.0 g (0.054 mole) of a 31.0% aqueous sodium hypochlorite solution are added in one hour, whereupon heating is continued at the same temperature, under stirring for 3 hours. The reaction mixture is further treated as described in Example 2 to yield 2.59 g of the aimed compound.
Yield: 84.0%
Melting point: 285° to 288° C.
Purity: 94.0%
$[\alpha]_D^{20} = -45.1°$ (c=1, 8:2 mixture of chloroform and methanol)

EXAMPLE 16

(−)-14-Hydroxyimino-eburnane(3α,16α) hydrochloride 1.5 g (0.00485 mole) of (−)-14-hydroxyimino-eburnane (3α,16α) are dissolved in 40.0 ml of dioxane at 60° to 70° C., and the pH of the solution is adjusted to 1 with hydrochloric acid in isopropanol.

Isopropanol is eliminated from the solution by distillation in vacuum, the distillation residue is cooled to 0° C. and the precipitated crystals are filtered off.

1.5 g of the desired compound are obtained.
Yield: 89.5%
Melting point: 304° to 307° C.
$[\alpha]_D^{20} = -51.5°$ (c=1, methanol)

EXAMPLE 17

(−)-14-Hydroxyimino-eburnane(3α,16α) citrate monoisopropanol solvate 1.5 g (0.00485 mole) of (−)-14-hydroxyimino-eburnane (3α,16α) are dissolved in 40.0 ml of dioxane at 60° C., and to the solution the solution of 1.05 g (0.005 mole) of citric acid monohydrate in 5 ml of methanol is added. The solution is then supplemented with 20.0 ml of diisopropyl ether and the precipitated crystals are filtered off. The crude product obtained is recrystallized from isopropanol to yield 1.7 g of the desired compound.

Yield: 61.8%

Melting point: 78° to 80° C.

$[\alpha]_D^{20} = -29.8°$ (c=1, methanol)

The new compounds are useful intermediates for producing known eburnamonines, especially vincamone, having higher antihypoxic activity than vincamine (Arzn. Forsch. 29 (8), 1094 (1979)). The eburnamonines can be made by treating the new eburnane derivatives of our invention with an acid (e.g. a mineral acid such as hydrochloric acid) in the presence of water as described, for example, in Hungarian application No. 1321/84.

We claim:

1. A compound of the formula (I)

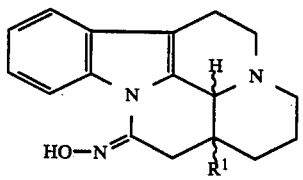

wherein $R^1$ is ethyl, or a pharmaceutically acceptable acid addition salt thereof.

2. A compound selected from the group consisting of
(−)-14-hydroxyimino-eburnane (3α,16α),
(+)-14-hydroxyimino-eburnane (3β,16β),
(+)-14-hydroxyimino-eburnane (3α,16β),
(−)-14-hydroxyimino-eburnane (3β,16α),
(±)-cis-14-hydroxyimino-eburnane,
(±)-trans-14-hydroxyimino-eburnane.

3. An anticonvulsive pharmaceutical composition comprising as active ingredient, a therapeutically effective amount of a compound of the formula (I) as defined in claim 1 or a pharmaceutically acceptable acid addition salt thereof in association with a carrier or excipient.

4. An anticonvulsive method of treatment which comprises the step of administering to a mammalian subject a therapeutically effective amount of the compound of the Formula (I) as defined in claim 1, or a pharmaceutically acceptable acid addition salt thereof.

5. A process for the preparation of a compound of the Formula (I)

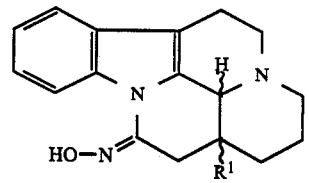

wherein $R^1$ is ethyl; or a pharmaceutically acceptable acid addition salt thereof, which comprises the step of oxidizing a compound of the Formula (II)

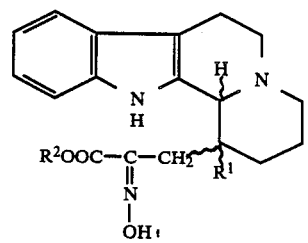

wherein $R^2$ is hydrogen or $C_1$ to $C_6$ alkyl, or a metal carboxylate salt or acid addition salt thereof, in an aqueous solution of an alkali metal hydroxide or an alkaline earth metal hydroxide by passing an oxygen-containing gas therethrough at a temperature between 60° C. and 150° C.

6. The process defined in claim 5 wherein the oxygen-containing gas is oxygen gas.

7. The process defined in claim 5 wherein the oxygen-containing gas is an inert gas mixture containing oxygen.

8. The process defined in claim 5 wherein the oxygen-containing gas is air.

9. The process defined in claim 5 which further comprises employing hydrogen peroxide as an oxidizing agent.

10. The process defined in claim 5 which further comprises employing a catalytically effective amount of a copper or manganese salt as an oxidation catalyst.

11. The process defined in claim 10 wherein the copper salt is copper acetate and the manganese salt is manganese acetate.

12. A process for the preparation of a compound of the Formula (I)

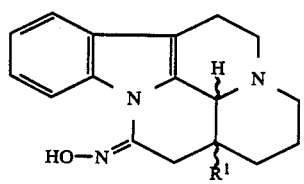

wherein $R^1$ is ethyl; or a pharmaceutically acceptable acid addition salt thereof, which comprises the step of oxidizing a compound of the Formula (II)

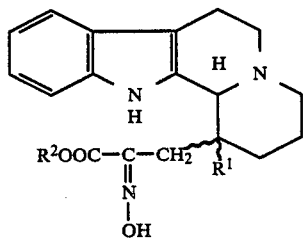

wherein $R^2$ is hydrogen or $C_1$ to $C_6$ alkyl, or a metal carboxylate salt or acid addition salt thereof, in an aqueous solution of an alkali metal hydroxide or alkaline earth metal hydroxide by adding hydrogen peroxide thereto at a temperature of between 60° C. and 150° C.

13. The process defined in claim 12 which further comprises employing a catalytically effective amount of a salt of copper or manganese as an oxidation catalyst.

14. The process defined in claim 13 wherein the salt of copper is copper acetate and the salt of manganese is manganese acetate.

15. A process for the preparation of a compound of the Formula (I)

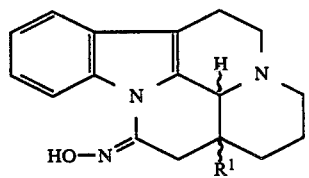

wherein
$R^1$ is ethyl; or a pharmaceutically acceptable acid addition salt thereof, which comprises the step of oxidizing a compound of the Formula (II)

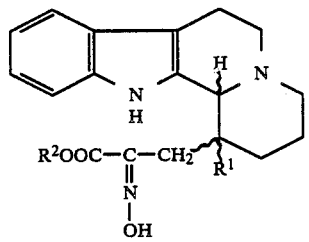

wherein $R^2$ is hydrogen or $C_1$ to $C_6$ alkyl, or a metal carboxylate salt or acid addition salt thereof, in an aqueous solution of an alkali metal or an alkaline earth metal hydroxide by employing a salt of copper or manganese as oxidizing agent in at least an equimolar amount at a temperature of between 60° C. and 150° C.

16. The process defined in claim 15 wherein the salt of copper is copper acetate and the salt of manganese is manganese acetate.

* * * * *